United States Patent
Unno et al.

(10) Patent No.: US 6,495,104 B1
(45) Date of Patent: Dec. 17, 2002

(54) INDICATOR COMPONENTS FOR MICROFLUIDIC SYSTEMS

(75) Inventors: Garrett Unno, San Jose; Colin B. Kennedy, Mill Valley, both of CA (US); Patrick Kaltenbach, Bischweier; Manfred Berndt, Waldbronn, both of (DE)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/377,681

(22) Filed: Aug. 19, 1999

(51) Int. Cl.[7] .................. G01N 15/06; G01N 27/36; B02L 3/00; B02L 3/02
(52) U.S. Cl. .............. 422/68.1; 422/99; 422/100; 204/601; 204/602
(58) Field of Search ................ 204/409, 600, 204/601; 422/99, 100, 82.01, 82.02, 82.03, 82.05, 68.1, 81

(56) References Cited

U.S. PATENT DOCUMENTS

| | | | |
|---|---|---|---|
| 4,390,403 A | 6/1983 | Batchelder |
| 4,908,112 A | 3/1990 | Pace |
| 5,126,022 A | 6/1992 | Soane et al. |
| 5,188,963 A | 2/1993 | Stapleton |

(List continued on next page.)

FOREIGN PATENT DOCUMENTS

| | | |
|---|---|---|
| WO | WO9533846 | 12/1995 |
| WO | WO9604547 | 2/1996 |
| WO | WO9702357 | 1/1997 |
| WO | WO-9721090 | * 6/1997 |
| WO | WO97/44132 | 11/1997 |
| WO | WO9805424 | 2/1998 |
| WO | WO-9850154 | * 11/1998 |

OTHER PUBLICATIONS

Cohen, C.B. et al., "A Microchip–Based Enzyme Assay for Protein Kinase A", *Anal. Chem.* (1999) 273:89–97.

Dasgupta, P.K. et al., "Electroosmosis: A Reliable Fluid Propulsion System for Flow Injection Analysis," *Anal. Chem.* (1994) 66:1792–1798, month unknown.

Jacobson, S.C. et al., "Fused Quartz Substrates for Microchip Electrophoresis," *Anal. Chem.* (1995) 67:2059–2063.

(List continued on next page.)

*Primary Examiner*—Jill Warden
*Assistant Examiner*—Alex Noguerola
(74) *Attorney, Agent, or Firm*—Matthew B. Murphy; Andrew L. Filler

(57) ABSTRACT

Microfluidic devices and systems that include keying, registration or indication elements that communicate a functionality of the microfluidic device to the instrumentation which is used in conjunction with these devices. Indicator elements include structural indicators, electrical indicators, optical indicators and chemical indicators. Different indicator elements are indicative of different functionalities, e.g., applications, new vs. used, and the like.

33 Claims, 8 Drawing Sheets

U.S. PATENT DOCUMENTS

| | | |
|---|---|---|
| 5,223,219 A | 6/1993 | Subramanian et al. |
| 5,498,392 A | 3/1996 | Wilding et al. |
| 5,571,410 A | 11/1996 | Swedberg et al. |
| 5,585,069 A | 12/1996 | Zanzucchi et al. |
| 5,593,838 A | 1/1997 | Zanzucchi et al. |
| 5,603,351 A | 2/1997 | Cherukuri et al. |
| 5,635,358 A | 6/1997 | Wilding et al. |
| 5,637,469 A | 6/1997 | Wilding et al. |
| 5,690,893 A * | 11/1997 | Ozawa et al. ............... 422/67 |
| 5,699,157 A | 12/1997 | Parce |
| 5,750,015 A | 5/1998 | Soane et al. |
| 5,779,868 A | 7/1998 | Parce et al. |
| 5,800,690 A | 9/1998 | Chow et al. |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,942,443 A | 8/1999 | Parce et al. |
| 5,945,334 A | 8/1999 | Basemer et al. |
| 5,948,227 A | 9/1999 | Dubrow |
| 5,955,028 A | 9/1999 | Chow |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |
| 5,965,410 A | 10/1999 | Chow et al. |
| 5,972,187 A | 10/1999 | Parce et al. |
| 5,976,336 A | 11/1999 | Dubrow et al. |
| 5,989,402 A | 11/1999 | Chow et al. |
| 6,001,231 A | 12/1999 | Kopf-Sill |
| 6,004,515 A | 12/1999 | Parce et al. |
| 6,011,252 A | 1/2000 | Jensen |
| 6,012,902 A | 1/2000 | Parce |

OTHER PUBLICATIONS

Manz, A. et al., "Electroosmotic pumping and electrophoretic separations for miniaturized chemical analysis systems," *J. Micromech. Microeng.* (1994) 4:257–265, month unknown.

Ramsey, J.M. et al., "Microfabricated chemical measurement systems," *Nature Med.* (1995) 1:1093–1096, Oct.

Seiler, K. et al., "Planar Glass Chips for Capillary Electrophoresis: Repetitive Sample Injection, Quantitation, and Separation Efficiency," *Anal. Chem.* (1993) 65:1481–1488, May.

Seiler, K. et al., "Electroosmotic Pumping and Valveless Control of Fluid Flow Within a Manifold of Capillaries on a Glass Chip," *Anal. Chem.* (1994) 66:3485–3491, month unknown.

* cited by examiner

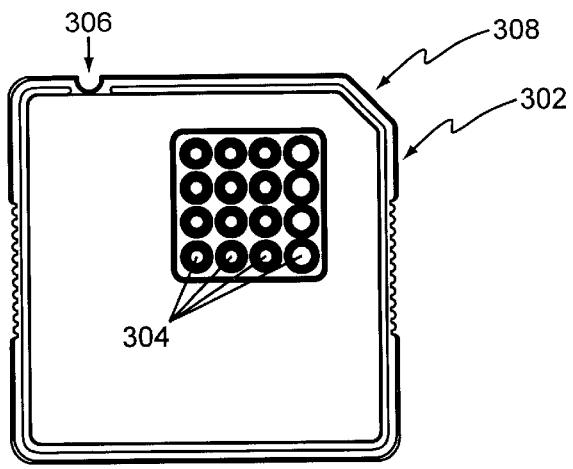
Fig. 3A-I
Fig. 3A-II
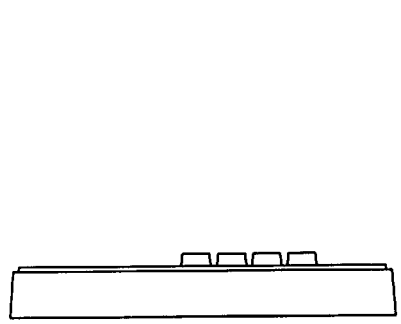
Fig. 3A-III
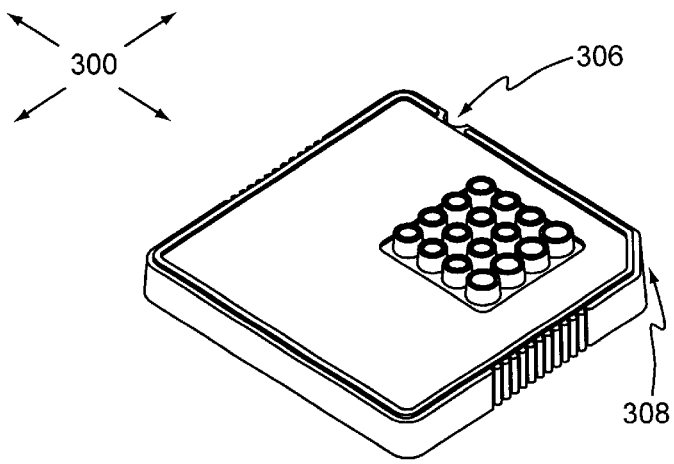
Fig. 3A-IV

INDICATOR COMPONENTS FOR MICROFLUIDIC SYSTEMS

BACKGROUND OF THE INVENTION

Microfluidic devices and systems have advanced rapidly from academic postulations to functioning commercial research products that are actively contributing to the research and development of pharmaceutical and other biotechnological and chemical products.

Examples of microfluidic devices and systems for performing a variety of different operations are described in, e.g., WO 98/00231, WO 98/05424, WO 98/22811, WO 98/46438 and WO 98/49548, all of which are incorporated herein by reference in their entirety for all purposes. Such microfluidic systems are generally configurable to perform virtually any operation, assay or experiment previously performed at the laboratory bench, but with a greater degree of accuracy, speed and automatability. Specifically, because microfluidic systems are performed in such small spaces, reagent quantities, an mixing times are substantially reduced. Further, because of the integrated nature of microfluidic systems, e.g., channel networks fabricated in a single chip, multiple different operations can be incorporated into a single device and controlled by an automated control and detection system. The availability of automated instrumentation, in turn, provides for unparalleled reproducibility as compared to bench scale operations, which rely upon measurements and judgements of human operators.

It is generally desirable to be able to automate more and more operations that are to be performed within a laboratory. While microfluidic systems, in general, contribute substantially to this automation desire, there exits a number of other operations that can be automated in conjunction with the use of these devices. The present invention provides apparatuses systems and methods that further contribute to this automation trend.

SUMMARY OF THE INVENTION

In a first aspect, the present invention provides a microfluidic device comprising a body structure configured to interface with a base instrument. The body structure includes microfluidic elements and an indicator element fabricated into the body structure. The indicator element provides an indication to an instrument of a functionality of the microfluidic device.

Another aspect of the present invention is a microfluidic system comprising a controller instrument. The controller instrument is comprised of a microfluidic device nesting region having an interface array for operably coupling one or more of a material transport system and a detector disposed within the controller instrument with a microfluidic device placed in the nesting region. The system also includes a microfluidic device having a body structure. The body structure includes an indicator element. The indicator element provides an indication to the instrument of a functionality of the microfluidic device.

BRIEF DESCRIPTION OF THE FIGURES

FIG. 3A–I shows a top view of a microfluidic device that includes a number of different registration elements as described herein. FIG. 3A–II is a side view of the microfluidic device of FIG. 3A–I. FIG. 3A–III is a side view of the microfluidic device of FIG. 3A–I. FIG. 3A–IV is a perspective view of the microfluidic device of FIG. 3A–I. FIG. 3B shows a view of a portion of the overall instrument including the interface portion that includes the device corral with one example of registration elements. FIG. 3C is an exploded view of the nesting region of an instrument similar to that shown in FIG. 3B, showing the registration elements.

DETAILED DESCRIPTION OF THE INVENTION

The present invention permits greater automatability by configuring the device to communicate one or more functionalities of the microfluidic device to instrumentation, and particularly controlling and/or detection instrumentation, to facilitate the operation of the combination of the device and instrumentation.

As used herein, a "functionality" of a microfluidic device refers to the use to which the device will be or has been put. The indicated functionality of a device may range from the relatively general, e.g., for performing multi-sample separations, to more specific, e.g., performing kinetic assay on a protein kinase sample. Thus, as typically used, the functionality refers to the application for the device. However, the term "functionality" as used herein, also includes whether device is functional for any application in the first instance, e.g., whether the device is nonfunctional as a previously used device.

Typically, from application to application, microfluidic devices and systems rely upon many of the same means to carry out the desired operation, e.g., in fluid or material movement, mixing etc., as well as detection of operation results. As such, instrumentation for operating these systems is generally standardizable, with the devices themselves, the chemistries placed in those devices, and the timing of reagent mixtures yielding distinctions between different operations.

For these standard instruments, different operating parameters, e.g., for performing different operations must generally be preprogrammed into the instrument or computers that control operation of the instruments. Of course it is still incumbent upon the user to identify for the instrument when a different application is to be performed. In accordance with the present invention, however, a microfluidic device is configured with an indicator element which indicates to the instrument the functionality of the device that is interfaced with the instrument, e.g., the specific type of assay or other application that is to be performed, or whether the device has been previously used. The instrument then typically adjusts for carrying out the operation of the device interfaced with it. For example, the instrument may select from different available detection modes, e.g., fluorescence wavelengths, UV transmittance, etc., as well as different available material transport means, e.g., pressure based fluid transport, electrokinetic transport or hybrid pressure/electrokinetic systems. For specifically identified functionalities, e.g., specific separations, enzyme assay or the like, the instrument also optionally implements control profiles, e.g., a script for directing fluids or other materials through specific channels at specific times and/or in specific ratios, volumes and/or flow rates.

Figure 1:
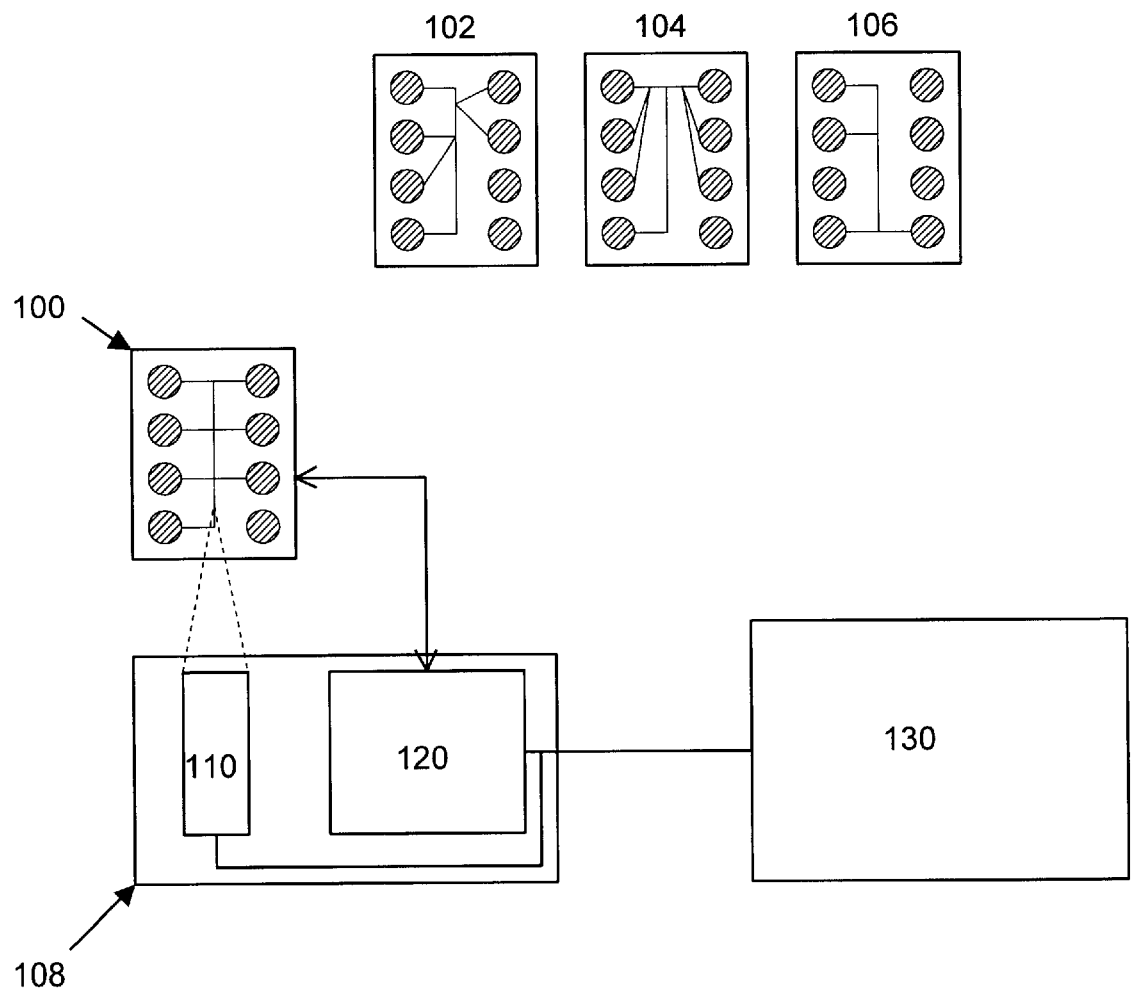
FIG. 1 schematically illustrates an overall microfluidic analysis system.

An overall system including a microfluidic device and its associated instrumentation is illustrated in FIG. 1. As shown, the system includes a microfluidic device 100, which is selected from a menu of devices having different functionalities, e.g., devices 100–106. As described in greater detail below, the microfluidic device typically includes an indicator element to communicate to the instrumentation of the system the functionality of that device. The system also typically includes a controller detector instrument 108, upon or into which the device is placed for operating the device. Once mounted on the instrument, detector 110 is disposed adjacent to the device 100 and within sensory communication of the channels disposed in the device, in order to detect results of reactions within those channels. As used herein "within sensory communication" refers to a detector that is positioned to receive a signal from a channel of the microfluidic device, typically at a detection window. Such signals include optical signals, thermal signals, electrical signals, and the like. In each case, the detector is placed such that the detection aspect of the detector, e.g., a sensor, is placed so as to receive the appropriate type of signal from the channel. In the case of optical signals, the detector is typically placed adjacent to a transparent region of the channel with the optical elements positioned to receive an optical signal and detect that signal. In the case of electrical detectors, a sensor is typically disposed within the channel in order to be within sensory communication.

Controller 120, also disposed in the instrument 108, controls the movement of materials through the channels and/or chambers of the microfluidic device in order to carry out the device's prescribed functionality. A computer or processor 130 is also typically provided to instruct the operation of the controller 120 in response to user input or programmed commands. The computer 130 also typically receives data from the detector 110, stores and/or analyzes the data to provide information to the user in a readily understandable format. Although illustrated as a separate element, it will be appreciated that the computer or processor 130 may be integrated into the instrument 108 as well.

As used herein, a "microfluidic device" refers to a device that includes at least one fluidic element, e.g., channel, chamber, reservoir or the like, that has at least one cross sectional dimension in the microscale range, e.g., between about 0.1 and about 1000 $\mu$m. Typically, such devices include networks of channels and/or chambers that are interconnected, and through which a variety of different fluids or other materials are transported. These devices are used to mix, separate, react and otherwise manipulate sample reagents and other materials in performing a variety of chemical, biochemical and biological analyses. Microfluidic devices may be fabricated in a variety of different ways. For example, a device may be fabricated as an aggregation of different parts, e.g., capillaries, reaction chambers, etc., that are pieced together to form a desired network of channels and/or chambers. In preferred aspects however, microfluidic devices are assembled from an aggregation of planar layers to form a single integrated microfluidic device that includes the channels and chambers within its interior portion.

Figure 2:
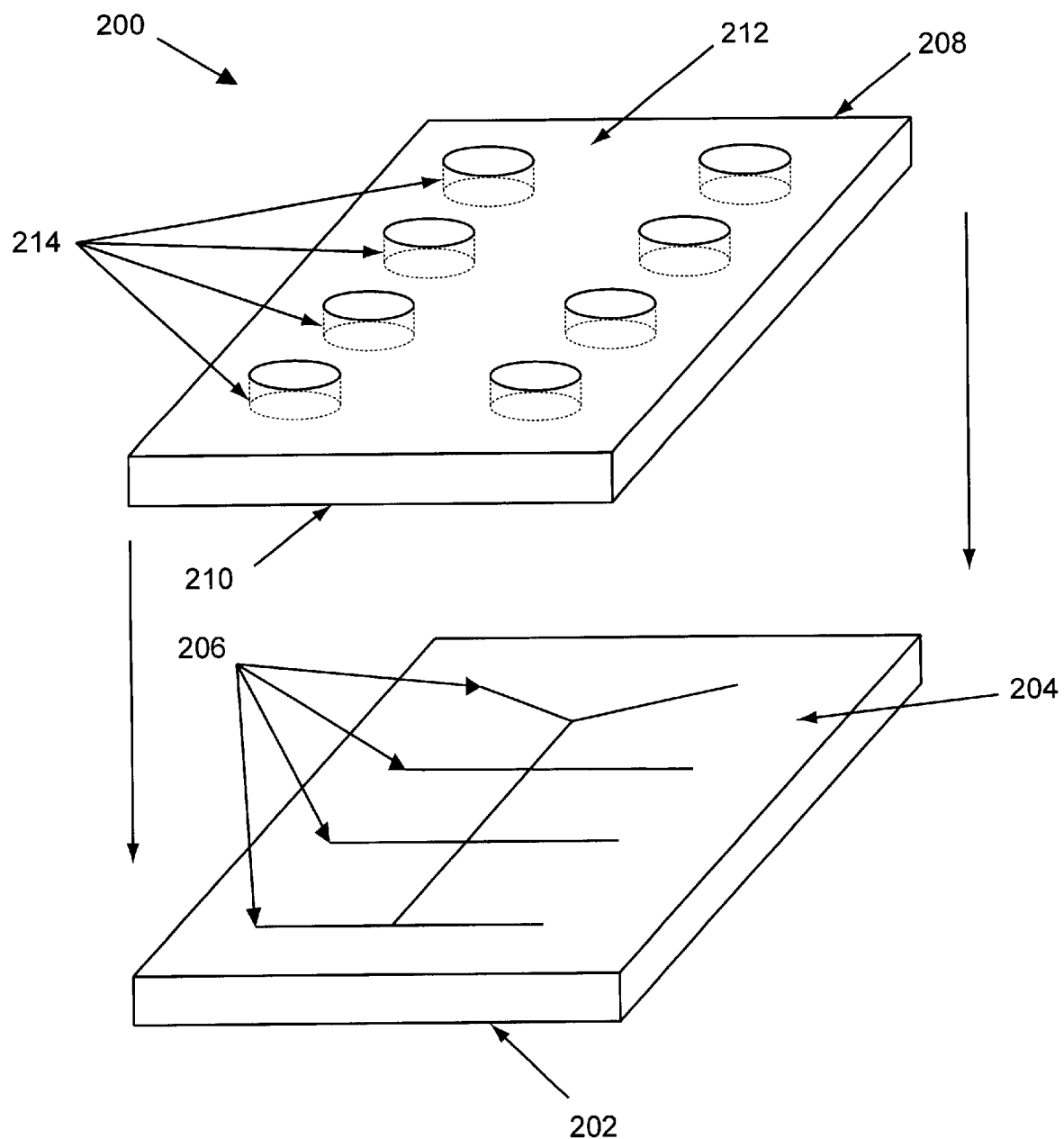
FIG. 2 schematically illustrates a microfluidic device.

One example of a microfluidic device is illustrated in FIG. 2. Specifically, FIG. 2 illustrates the layered construction of preferred microfluidic devices. As shown, the device body structure 200 is fabricated from two or more layers 202 and 208. In particular, the bottom portion of the device 202 comprises a solid substrate that is substantially planar in structure, and which has at least one substantially flat upper surface 204. The channels and/or chambers of the microfluidic devices are typically fabricated into the upper surface of the bottom substrate or portion 202, as microscale grooves or indentations 206, using the above described microfabrication techniques. The top portion or substrate 208 also comprises a first planar surface 210, and a second surface 212 opposite the first planar surface 210. In the microfluidic devices prepared in accordance with the methods described herein, the top portion also includes a plurality of apertures, holes or ports 214 disposed therethrough, e.g., from the first planar surface 210 to the second surface 212 opposite the first planar surface.

The first planar surface 210 of the top substrate 208 is then mated, e.g., placed into contact with, and bonded to the planar surface 204 of the bottom substrate 202, covering and sealing the grooves and/or indentations 206 in the surface of the bottom substrate, to form the channels and/or chambers (i.e., the interior portion) of the device at the interface of these two components. The holes 204 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

These devices may be used in a variety of applications, including, e.g., the performance of high throughput screening assays in drug discovery, immunoassays, diagnostics, genetic analysis, and the like, e.g., as described in Published International Patent Application No. 98/00231 and U.S. Pat. No. 5,779,868 each of which is hereby incorporated by reference in its entirety for all purposes.

Indicator elements fabricated or otherwise disposed within a microfluidic device may take on a variety of forms, including mechanical indicator elements, electrical indicator elements, optical indicator elements and chemical indicator elements. The specific type of indicator element used in a particular device is mirrored by a complementary detection element upon the instrument which is interfaced with the device.

Mechanical indicator elements typically comprise a registration structure or collection of registration structures or structural elements fabricated onto, into or attached to the body of the microfluidic device. The registration structures on the device mate with or otherwise engage elements upon the nesting region of an instrument. The elements upon the instrument may include complementary registration structures which are configured only to receive the registration structures of a particular device, e.g., having a specific application. In such cases, only one type of device will be permitted to interface with the nesting region or adapter element of the instrument, as other devices will not possess the same complementary registration elements or structures. In order to interface a different device with the instrument, one is required to swap out the adapter element/nesting region for an adapter having the appropriate registration structures. The use of interchangeable adapter elements for interfacing different microfluidic devices to a common instrument platform has been previously described in, e.g., published International Patent Application No. WO 98/05424, which is incorporated herein by reference in its entirety for all purposes.

A variety of registration or indicator structures are optionally employed in this aspect of the present invention. For example, a series of pins, posts, blocks, tabs, etc. may be disposed upon the surface of the nesting region of the instrument. A corresponding and complementary series of holes, depressions, notches, cavities are then disposed on the device to receive the structures on the instrument when the microfluidic device is appropriately oriented on the nesting region. Although described as positive structures, e.g., protrusions, being disposed on the instrument and negative structures, e.g., depressions, being disposed on the microfluidic device, it will be appreciated that the complementary structures may be disposed upon either the device or the instrument.

Alternatively or additionally, the microfluidic device may incorporate at least one shaped edge, e.g., having a unique contour, that is complementary to an edge of the nesting region, such that absent the appropriately shaped edge, the microfluidic device will not be insertable into the nesting region of the instrument.

Figure 3B:
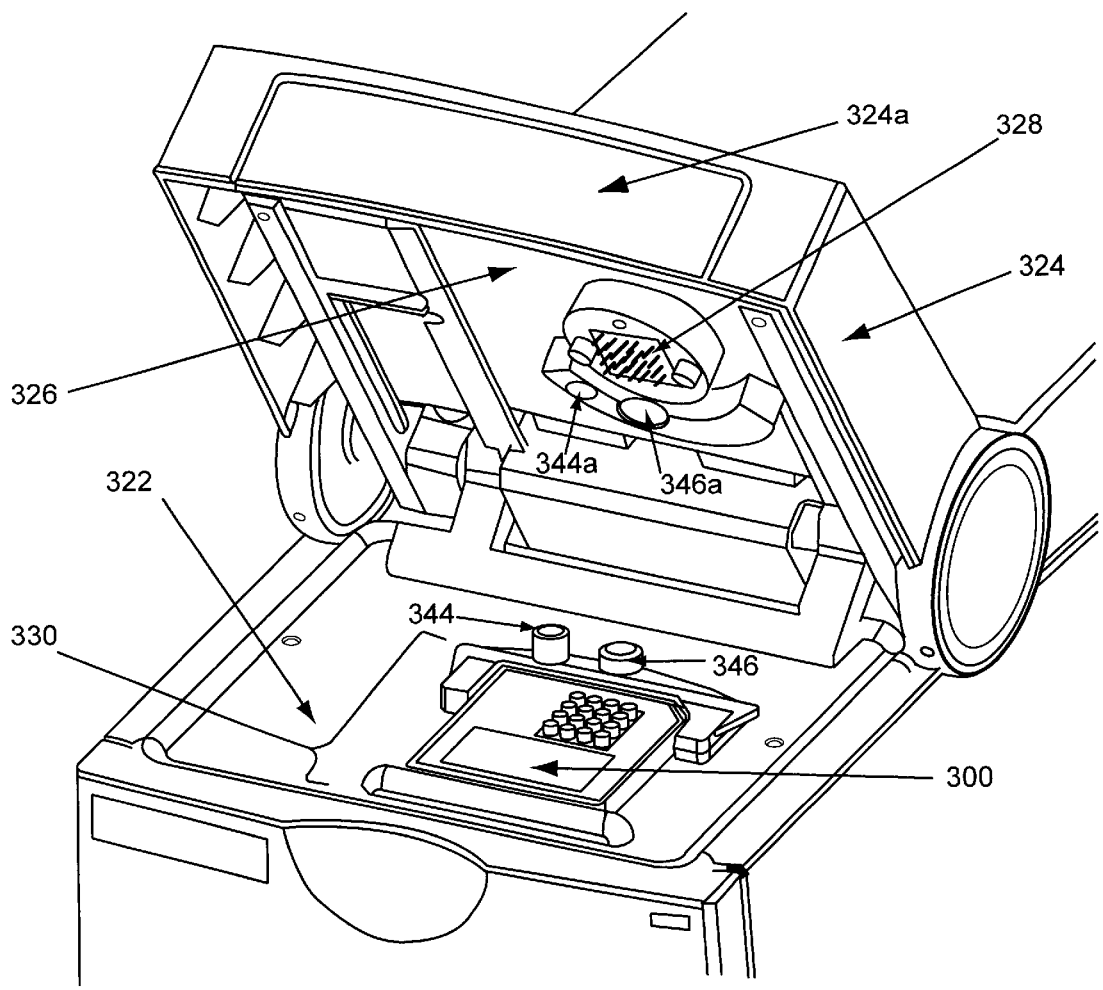
Figure 3C:
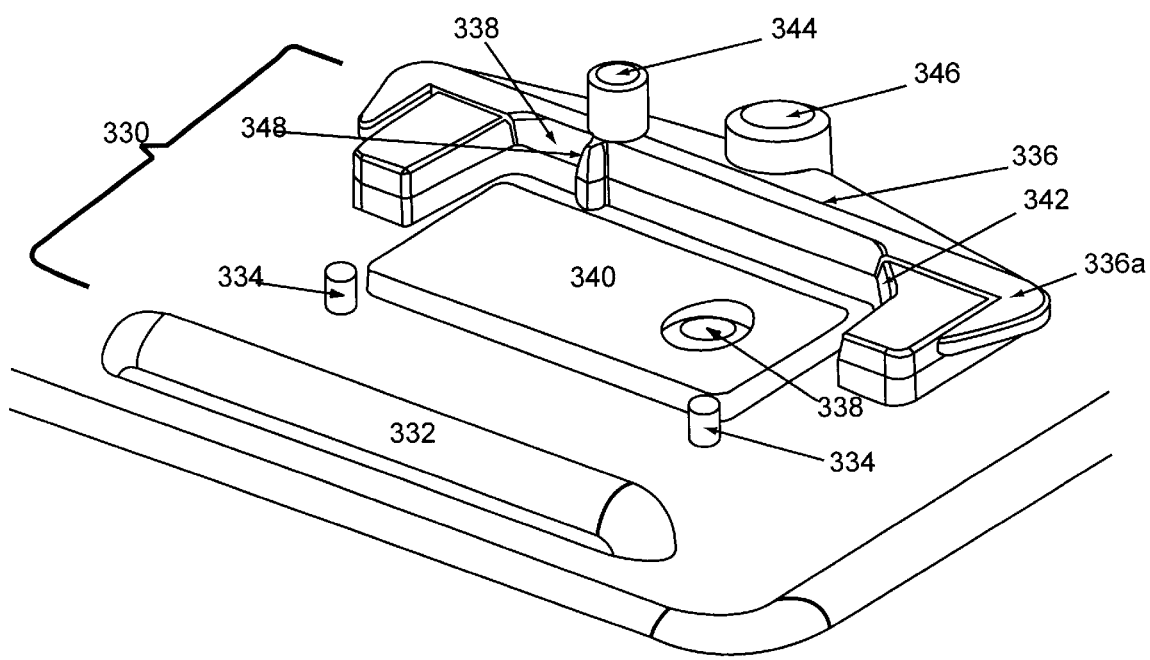

FIG. 3 schematically illustrates an example of a registration/indicator structure on a microfluidic device and its controller/detector instrument. FIG. 3A illustrates the microfluidic device 300 that includes a number of exemplary registration structures, from a number of views (top (FIG. 3A–I), side (FIG. 3A–II), end (FIG. 3A–III) and perspective (FIG. 3A–IV)). As shown, the device 300 includes a body structure 302 which includes a microfluidic substrate attached or integral thereto (not shown). The body structure includes ports or reservoirs 304 disposed thereon which are in fluid communication with the channel elements of the microfluidic device. The body structure of the device also includes a number of registration structures, e.g., notch 306 and truncated corner 308, which provide an indication of the functionality of the microfluidic device, e.g., the particular application for which the device is used, i.e., nucleic acid separations, protein separations, enzyme assays, cellular function assays and the like. Specifically, the position, number and or size of the registration structures is typically varied from a device of one functionality to a device of another functionality. For example, although illustrated with a single notch 306 along one edge of the body structure 302, multiple notches, or different size notches are optionally used along the same edge or different edges of the body structure to identify the functionality of the overall device.

A complementary structure or set of structures on the instrument is used to ensure that the instrument is appropriately configured to interface, control and monitor the functionality, e.g., the application, of the microfluidic device inserted therein. FIG. 3B illustrates a portion of an example of a controller detector instrument 320 that includes a nesting region 322 onto which the device 300 is mounted.

A lid 324 is rotatably attached to the instrument 320. The underside of the lid 326 typically includes a number of interface elements for controlling the functioning of the device. For example, as shown, a plurality of electrodes 328 are provided attached to the underside 326 of the lid 324. These electrodes 328 rotate into communication with fluids in the reservoirs 304 in the body structure of device 300. These electrodes 328 that are operably coupled to power sources (not shown) within the instrument 320, provide actuation of material movement within the channels of the device 300 via electrokinetic forces. Although shown as electrodes 328, other interfaces are optionally or additionally provided in the lid. For example, in certain preferred aspects, one or more vacuum or pressure ports are provided in the lid with appropriate connectors for interfacing with one or more reservoirs 304 of the device 300, in order to provide material movement by pressure induced flow. These vacuum or pressure ports are operably coupled to vacuum or pressure pumps disposed within the instrument 320. As shown, at least a portion of the lid 324 is removable and replaceable, in order to reconfigure the instrument to interface with a wide range of different devices. In particular, interface cassette 324a, which includes the array of electrodes 328, is removable from lid 324, and a different cassette may be inserted in its place. This three-tier instrument architecture (e.g., device, instrument and removable interface adapter) is described in detail in Published International Patent Application No. WO 98/05424, which is incorporated herein by reference.

FIG. 3C shows an exploded view of a nesting region shown in FIG. 3B, absent a microfluidic device. As shown, the nesting region 322 includes a microfluidic device "corral" 330 which functions to both orient the device 300 upon the nesting region, and ensure that the instrument 320 is appropriately configured for the functionality of the device 300. Orientation of the device is provided, inter alia, by a number of structures on the nesting region, including barrier 332, alignment pins 334, and barrier 336. The presence of these orientation structures ensures that a device 300 placed into the nesting region 322 is appropriately positioned such that the collection lens 338 of a detector disposed in the instrument (not shown) is placed adjacent to and in sensory communication with a relevant channel of the microfluidic device 300. Proper orientation is also desirable to provide for proper interfacing of other elements of the instrument with the microfluidic device, e.g., heating element or heat sink 340, and flow actuation elements in the lid 324, e.g., electrodes 328.

As shown, barrier 336 includes additional structural elements that are used to both align the device 300 in the nesting region 322, as well as provide an indication of the functionality of the device 300 to be used, e.g., which the instrument is configured to run at a particular given time. In particular, the interior edge 338 of barrier 336 defines one boundary of corral 330 against which a microfluidic device is positioned. As shown, a first tab 348 is provided extending into the corral 330. The tab 348 is positioned and sized to fit within the notch 306 that is disposed along the edge of the microfluidic device 300. The interior edge 338 of barrier 336 also defines a truncated corner 342 that corresponds and is complementary to the truncated corner 308 of device 300. As shown, barrier 336 also includes structural registration elements that communicate the functionality of the device to the instrument. In particular, posts 344 and 346 are disposed on barrier 336. These posts are positioned and sized (e.g., diameter, height etc.) to indicate the particular functionality of the microfluidic device to which they are applied. As shown, post 344 is thinner and taller than post 346. With reference to FIG. 3B, these posts 344 and 346 are positioned to mate with corresponding apertures or cavities 344a and 346a, respectively, in interface cassette 324a or optionally lid 324. The complementary nature of posts 344, 346 and cavities 344a and 346a, ensures that the interface cassette 324a inserted into lid 324 is appropriate for the particular device 300, as indicated by the registration structures on barrier 336, e.g., notch 306, and posts 344 and 346. In preferred aspects, a portion or all of barrier 336 is removable (e.g., barrier portion 336a), allowing for substitution with a barrier that includes different registration elements, e.g., numbers and sizes of notches, posts and the like. In operation, microfluidic devices having different functionalities include different registration structures on their body structure, which registration structures are indicative of the functionality of the device. When a device having a different functionality is to be run on an instrument, one replaces the barrier 336 with a new barrier having registration structures complementary to the functionally desired device, and also substitutes the interface cassette with an appropriate interface for the new device, e.g., electrode configuration, vacuum or pressure ports, etc. Certain of the registration structures on the cassette 324a and barrier 336 cooperate to ensure that both the cassette and the barrier are appropriate for the device to be run. Improper cooperation of these elements can lead to damaging of elements of the device and/or the interface cassette, e.g., bending electrodes, damaging optics, etc. Proper alignment of the microfluidic device in the nesting region is shown in FIG. 3D.

Thus, in accordance with the above-described aspect of the present invention, "indication of a device's functionality to the instrument" is provided by an ability to close lid 324 over the device 300, e.g., improper interfacing of a device and an instrument is prevented by structural interference of one or more of the registration elements, e.g., as between device 300 and barrier 336 and/or between barrier 336 and interface cassette 324a. Thus, this "indication" encompasses both more active communication between the device and the instrument, as described in greater detail herein, as well as passive communication, e.g., as described with reference to FIG. 3.

Figure 4:
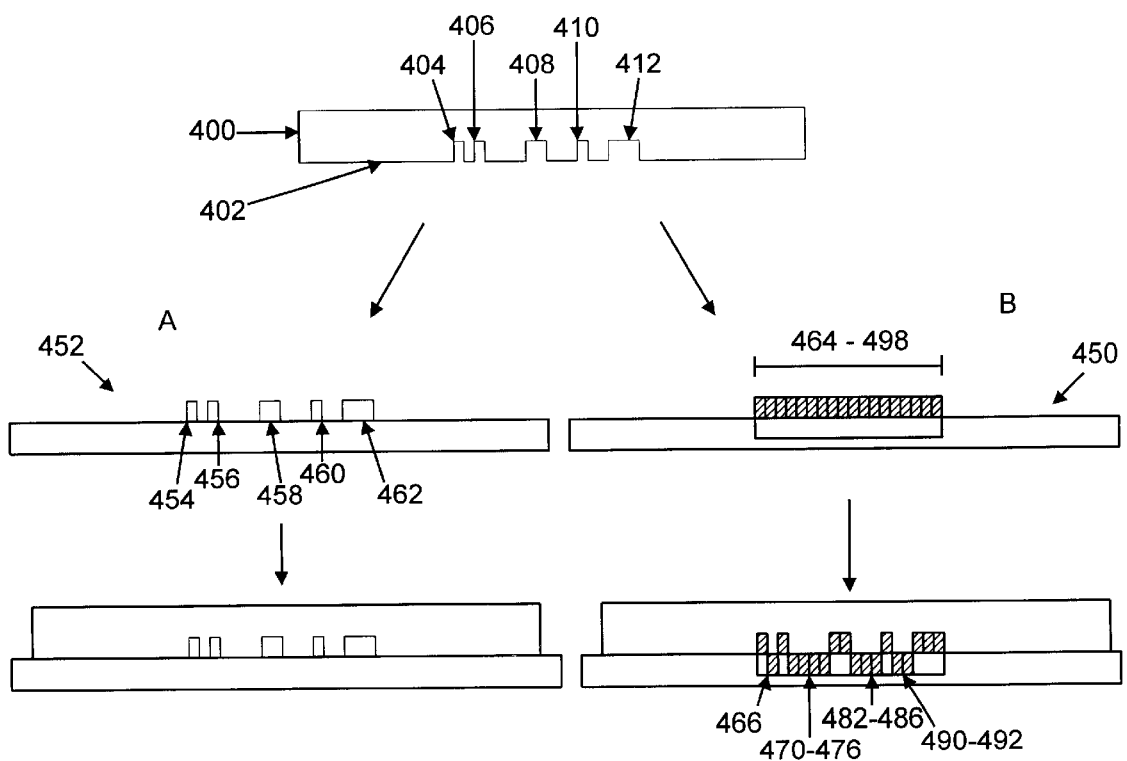
FIG. 4 is an alternate schematic illustration of a microfluidic device and accompanying instrument that comprise mechanical indicator elements/registration structures.

FIG. 4 schematically illustrates alternate examples of a microfluidic device having mechanical indicator or registration elements, as described herein. As shown, a microfluidic device body structure 400 (shown from a side view), is provided having a series of notches 404–412 disposed in its lower surface 402. The arrangement, size and shape of these notches 404–412 is selected depending upon the particular application or functionality of the microfluidic device. For example, as shown, the body structure includes narrow notches 404, 406 and 410 and wider notches 408 and 412. The notches 404–412 on the body structure 400 correspond and are generally complementary to registration structures disposed upon the nesting region 452 of a controller/detector instrument (not shown). As shown, these registration structures include, e.g., posts 454–462, which are provided in a position and of a size such that when the body structure is placed upon the nesting region, the notches 404–412 engage or receive the posts in a fitted fashion, securing the body structure in position, e.g., as shown in Panel A. Further, interaction among these two elements is only generally possible where these structures are complementary. As a result, the functionality of the microfluidic device, e.g., as indicated by the indicator structures, is communicated to the instrument through the inclusion of a proper nesting region 452, e.g., in an appropriate adapter element.

Optionally, the elements on the instrument that are engaged by the registration elements comprise displaceable elements that are displaced by the registration structures on the device (or are not displaced where the registration structure comprises a notch, slot, groove or cavity). Specifically, such elements typically comprise pins, tabs or other structures within the nesting region of the device, that are spring mounted such that they are normally extended into the nesting region of the device, but whereby presence of the device in the nesting region displaces some or all of these elements. Typically, these displaceable elements are also operably coupled to the control or processor elements of the instrument, whereby displacement of an element is detected by the instrument, e.g., through the completion or breaking of an electrical circuit within the instrument. The identity and number of the plurality of these displaceable elements that is displaced by the registration structures of a particular device serves as an identification code for that device. In this manner, the registration structures on the device function as a key which, based upon the identity and number of elements displaced, indicates to the instrument, the functionality of the microfluidic device.

This alternative aspect is shown in Panel B of FIG. 4. Specifically, the registration structures on the nesting region 452 comprise an array of movable or displaceable elements, e.g., posts 464–498, which are deflectable upon interaction with the indicator structures on the body structure 400. For example, as shown, the nesting region 450 includes an array of deflectable posts 464–498 extending into the nesting region. When a device's body structure 400 is placed onto the nesting region, the indicator structures on the body 400, e.g., notches 404–412 deflect the posts in a pattern reflective of those indicator structures, e.g., only posts 66, 72–76, 82–86 and 90–92 are deflected. The deflection or lack of deflection of each post is detected by the instrument. As a result, the functionality of the device, as indicated by the arrangement, size and position of notches (or other indicator structures), is communicated to the instrument by virtue of the number and identity of the posts that are deflected by the body of the device. In this latter aspect, the "indication" of a device's functionality is more of an active communication between the device and the instrument, e.g., by virtue of the device's active deflection of certain structures ("switches") on the instrument. The instrument then configures itself, e.g., via software or firmware programming, to run the device mounted thereon.

In alternate aspects, the indicator elements fabricated into or otherwise disposed on or within the microfluidic devices, comprise electrical indicator elements. The electrical indicator elements described herein may be passive or active electrical elements. In preferred aspects, the electrical indicators are passive, e.g., having no internal power supply such as a battery, due to the costs associated with such systems. While not preferred, it will be appreciated that active electrical indicator elements are also envisioned within the scope of the present invention.

Typically, electrical indicator elements comprise one or more electrical circuits disposed on or within the body of the microfluidic device. The electrical circuits are typically oriented to contact two or more electrical contacts disposed upon the nesting region of the controller instrument, so as to complete an electrical circuit between the two or more contacts. The indicator function of the electrical indicator elements is optionally provided by the number and identity of different circuits that are completed when the device is inserted into the nesting region. Specifically, the pattern of electrical circuits connects a distinct set or subset of electrical contacts in the nesting region to yield an electrical signature that is indicative of the functionality of the device used. Alternatively, the specific resistance or conductivity of the electrical circuits on the device is varied among different devices, such that this resistance level comprises the electrical signature that is indicative of the functionality of the device.

Fabrication of electrical circuits into or on a device's body may be accomplished by a number of means. For example, in some aspects, simple patterned metal layers are disposed upon an outer surface of the body so as to contact a preselected subset of electrical contacts disposed upon the nesting region, thereby yielding a preselected electrical signature when a current is applied to the electrical contacts. Alternatively, integrated circuits may be attached to or disposed within the body structure of the device. Such integrated circuits generally permit a greater complexity of available electrical signatures using combinations of specific circuits and relative resistances to provide the signature.

In certain aspects, an electrical indicator element may provide an indication to the instrument as to whether the microfluidic device has been previously used or the nature of any previous use. As a result of a previously used device, an instrument may refuse to operate, or it may prompt the user as to the desirability of using a previously used device. In a preferred aspect, this type of electrical indicator element comprises one or more electrical circuits, e.g., as described above, except that one or more of the circuits functions as a modifiable fused link. In operation, following the use of the device, the instrument sends a programmed electrical surge or other signal through the circuit or circuits of interest, resulting in modification of the fused link and of the electrical circuit. For example, such fused links may be severable via the electrical signal, resulting in severance of the electrical circuit. In multi-use devices, several such links may be provided, each being severed after a subsequent use, until the recommended number of uses has been carried out. Alternatively, such fuses may be simply modified via the electrical signal, e.g., having an altered electrical signal, e.g., resistance or the like.

Figure 5:
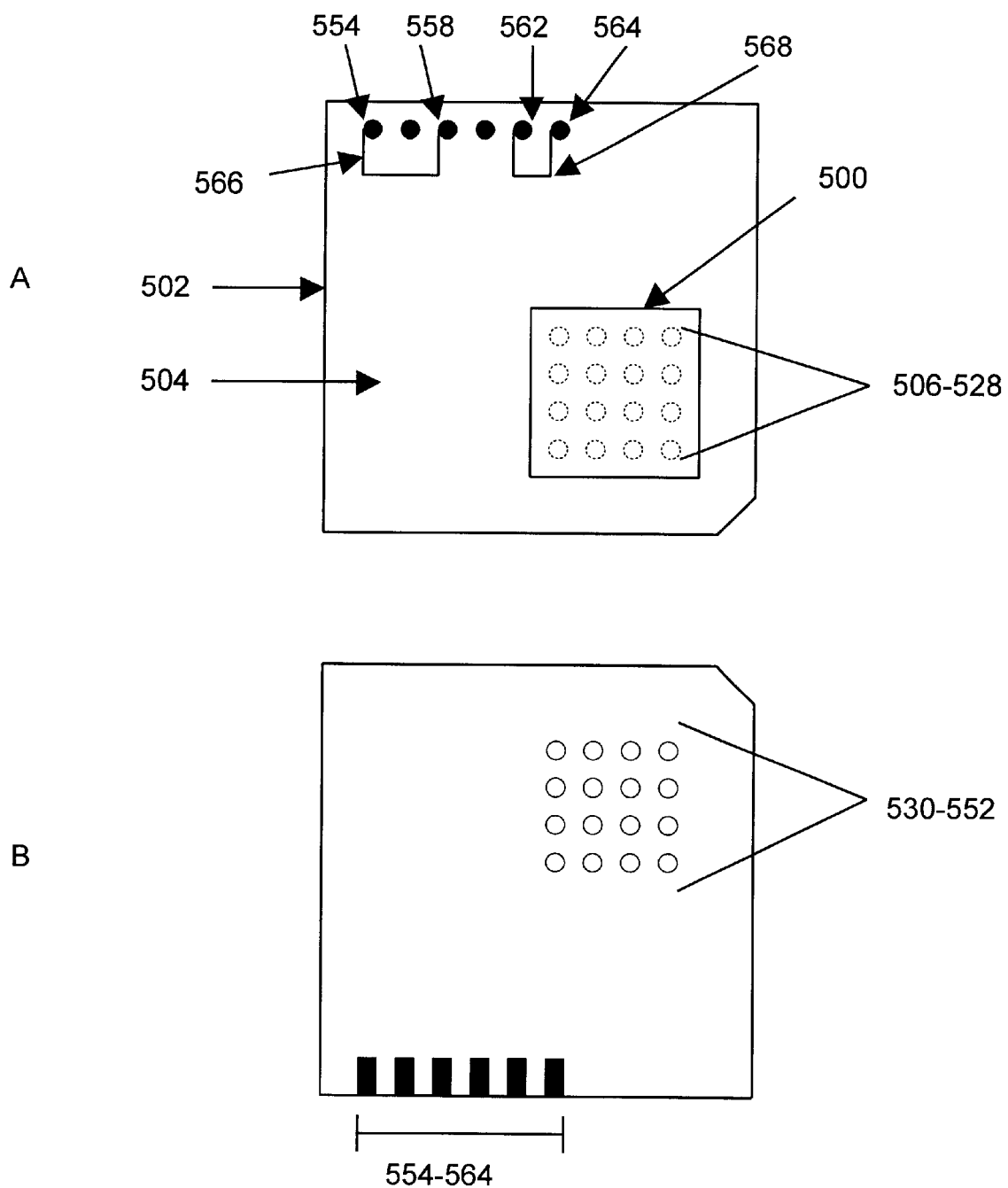
FIG. 5 schematically illustrates one example of a microfluidic device incorporating an electrical indicator element according to the present invention.

One example of an electrical indicator element is illustrated in FIG. 5. As shown, a microfluidic device 500 is provided attached to the bottom surface 504 of a holder assembly 502 (see U.S. patent application Ser. No. 09/028, 965, filed Feb. 28, 1994) which doubles as an overall body structure. The reservoirs 506–528 of the device 500 communicate via ports 530–552 to the upper surface of the holder assembly 504. As shown, the holder assembly 502 includes an array of electrical contact pads 554–564. These contact pads are positioned to contact a similar set of contact pads in the nesting region of a controller/detector instrument (not sown).

Upon the body structure/holder assembly 502, electrical circuits, e.g., circuits 566 and 568, are provided connecting different pairs or sets of the electrical contact pads 554–564. As shown, these circuits 566 and 568 comprise metal patterns that are fabricated onto the bottom surface 504 of the holder assembly 502. When inserted into the nesting region, the instrument, via its electrical contact pads, applies a low level current through the electrical circuits 566 and 568, on the holder assembly 502. The specific pattern of the electrical circuits is identified by the instrument, e.g., by virtue of the presence or absence of current between two separate contact pads, the level of resistance of those circuits, or both. By way of example, in the device shown in FIG. 5, an electric current could be applied between contact pads 554 and 558, e.g., via circuit/wire 566, and between pads 562 and 564, via circuit/wire 568. However no other currents could be applied or detected due to the lack of an existing circuit. Additionally or alternatively, the electrical resistance in the existing circuits is optionally varied as an indicator function. This increases the variability of the signaling function.

As noted above, one or more of the electrical circuits, e.g., wires 566 and 568 comprises a fused link. Such fused links are generally provided such that a known level of electrical current will excessively heat the wire, resulting in its melting and severing. These circuit compositions are well known to those of skill in the electronics arts.

Although illustrated as an array of contact pads connected by wires or metal traces, it will be appreciated that in preferred aspects, an integrated circuit is used to provide the electrical circuits on the body of the device. Specifically, the complexity of circuits available through IC technology allows substantially greater variability in an electrical indicator element. Further, such ICs are readily incorporated into the body of the devices of the invention, e.g., in the same fashion the microfluidic device substrate is attached to the holder assembly 502 in FIG. 5. Electrical interaction with the nesting region is then accomplished in the same fashion as shown in FIG. 5, or alternatively, through the inclusion of electrical connector pins, i.e., as typically used in the electronics industry for connecting ICs to circuit boards.

In a further aspect, the indicator element fabricated into or otherwise disposed on the body of the microfluidic device comprises an optical indicator element. As used herein, an optical indicator element is an element that is optically detected by the instrument. Again, as with the electrical indicator elements described above, optical elements may be passive or active, e.g., emitting detectable light levels. Typically, however, passive optical indicators are preferred. One example of a particularly preferred type of optical indicator element is a bar code that is affixed to or otherwise attached or fabricated onto the microfluidic device's body structure. Specifically, bar codes may be readily employed as indicators of the particular assay or other functionality of the microfluidic device being used. Instruments used in conjunction with those devices that incorporate include detection systems for detecting the optical indicator elements. In the case of bar codes, suitable and well known bar code readers are incorporated into the instrument and oriented to read the device's bar code from the body of a device inserted into the nesting region of the instrument.

Figure 6:
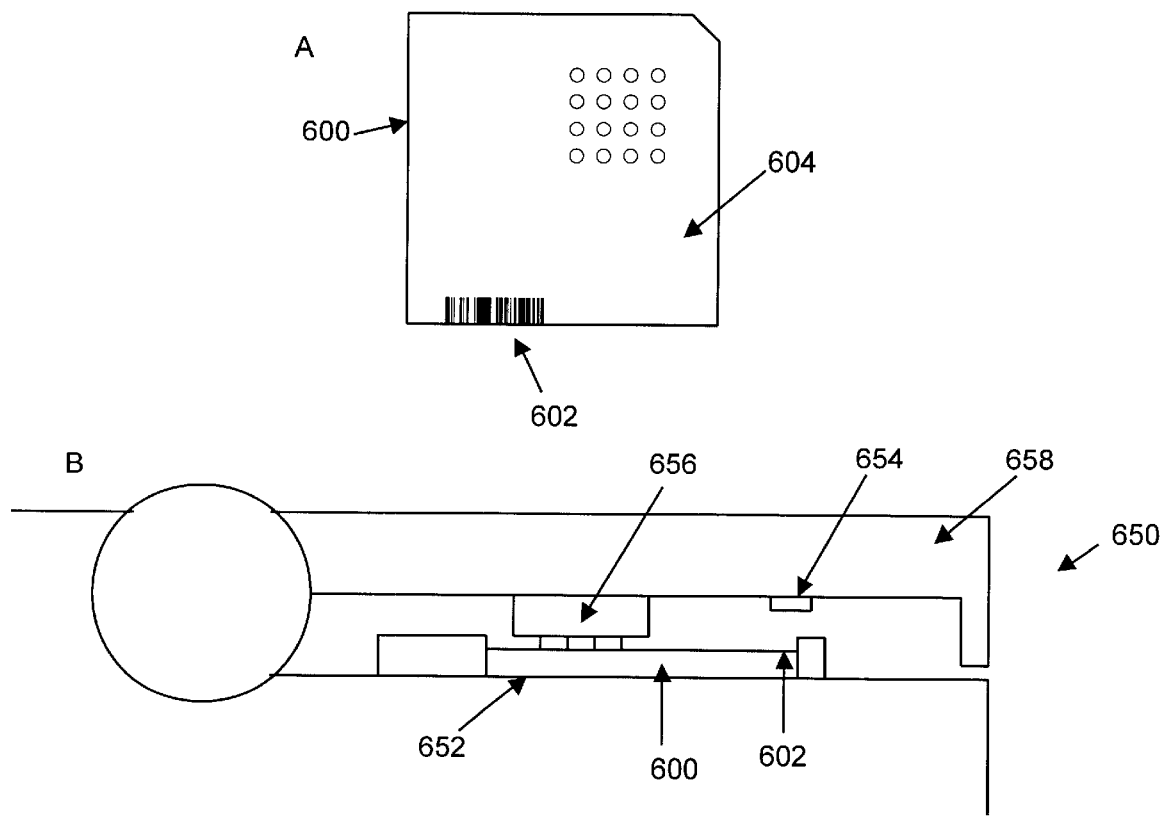
FIG. 6 schematically illustrates a microfluidic device including an optical indicator element and accompanying instrument.

An example of a device incorporating an optical indicator element is schematically illustrated in FIG. 6. As shown in panel A, the device 600 includes a bar code 602 disposed on an upper surface 604 of the device 600. As shown in panel B, when the device 600 is inserted into the nesting region 652 of an instrument 650, a detector 654 for optically detecting the bar code 602 is placed adjacent to the bar code 602. The detector 604 scans and detects the bar code and relays the information embodied within the code to the instrument 650, indicating the functionality of the device 600 to the instrument 650.

Examples of chemical indicator elements include reservoirs, wells or the like incorporating detectable chemicals, e.g., fluids having predefined ionic strengths, pH, and the like, which are indicative of a functionality of the device itself.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A microfluidic device, comprising:
 a body structure configured to interface with a base instrument, the body structure having microfluidic elements disposed therein; and an indicator element fabricated into the body structure, the indicator element providing an indication to an instrument of a functionality of the microfluidic device, and the indicator element being selected from, an electrical indicator element comprising one or more electrical circuits disposed on the microfluidic device, or a chemical indicator element.

2. The microfluidic device of claim 1, wherein the indicator element provides an indication as to whether the device has been previously used.

3. The microfluidic device of claim 1, wherein the indicated functionality of the microfluidic device is a specific application of the microfluidic device.

4. The microfluidic device of claim 3, wherein the indicated functionality comprises a specific assay type to be performed within the microfluidic device.

5. The microfluidic device of claim 1, wherein the indicated functionality of the microfluidic device comprises a desired flow control system for use with the microfluidic device.

6. The microfluidic device of claim 1, wherein the indicator element comprises an electrical indicator element, and the one more electrical circuits are embodied in an integrated circuit (IC) disposed in the body.

7. The microfluidic device of claim 1, wherein the indicator element comprises an electrical indicator element, and wherein the one or more electrical circuits comprises an electrical signature indicative of the functionality of the microfluidic device.

8. The microfluidic device of claim 7, wherein the electrical signature comprises a level of resistance through the one or more electrical circuits.

9. The microfluidic device of claim 1, wherein the electrical indicator element comprises an electrical indicator element, and the electrical indicator element comprises a modifiable electrical circuit, modification of the electrical circuit being indicative that the microfluidic device has been previously used.

10. A microfluidic device, comprising:
a body structure configured to interface with a base instrument, the body structure having microfluidic elements disposed therein; and
an indicator element fabricated into the body structure, the indicator element comprising a mechanical indicator element that comprises a registration structure that is complementary to a registration structure on the instrument, and the indicator element providing an indication to an instrument of a functionality of the microfluidic device.

11. The microfluidic device of claim 10, wherein the indicator element provides an indication as to whether the device has been previously used.

12. The microfluidic device of claim 10, wherein the indicated functionality of the microfluidic device is a specific application of the microfluidic device.

13. The microfluidic device of claim 12, wherein the indicated functionality comprises a specific assay type to be performed within the microfluidic device.

14. The microfluidic device of claim 10, wherein the indicated functionality of the microfluidic device comprises a desired flow control system for use with the microfluidic device.

15. A microfluidic device, comprising:
a body structure configured to interface with a base instrument, the body structure having microfluidic elements disposed therein; and
an indicator element fabricated into the body structure, the indicator element comprising a mechanical indicator element that comprises a registration structure, and providing an indication to an instrument of a functionality of the microfluidic device wherein the registration structure is identifiable by the instrument, thereby indicating the functionality of the microfluidic device to the instrument.

16. The microfluidic device of claim 5, wherein the indicator element providing an indication as to whether the device has been previously used.

17. The microfluidic device of claim 15, wherein the indicated functionality the microfluidic device is a specific application of the microfluidic device.

18. The microfluidic device of claim 17, wherein the indicated functionality comprises a specific assay type to be preformed within the microfluidic device.

19. The microfluidic device of claim 15, wherein the indicated functionality of the microfluidic device comprises a desired flow control system for the microfluidic device.

20. A microfluidic device, comprising:
a body structure configured to interface with a base instrument, the body structure having microfluidic elements disposed therein;
an indicator element fabricated into the body structure, the indicator element comprises an electrical indicator element comprising one or more electrical circuits disposed on the microfluidic device; and
wherein the one or more electrical circuits comprises an electrical signature indicative of the functionality of the microfluidic device the electrical signature comprising a number and identity of two or more electrical contacts on the instrument that are connected by the one or more electrical circuits on the microfluidic device.

21. A microfluidic system, comprising:
a controller instrument comprising a microfluidic device nesting region having an interface array for operably coupling one or more of a material transport system and detector disposed within the controller instrument with a microfluidic device placed in the nesting region; and
a microfluidic device having a body structure, the body structure comprising an indicator providing an indication to an instrument of a functionality of the microfluidic device, the indicator element being selected from an electrical indicator element comprising one or more electrical circuits disposed on the microfluidic device, or a chemical indicator element.

22. The microfluidic system of claim 21, wherein the indicator element provides an indication to the instrument of whether the microfluidic device has been previously used.

23. The microfluidic system of claim 21, wherein the indicator element comprises an electrical indicator element comprising one or more electrical circuits disposed on the microfluidic device.

24. The microfluidic system of claim 23, wherein the one or more electrical circuits comprises an electrical fuse that is electrically severable after use.

25. The microfluidic system of claim 23, wherein the one or more electrical circuits provide an electrical signature that is indicative of a functionality of the microfluidic device.

26. The microfluidic system of claim 25, wherein the electrical signature comprises a level of electrical resistance through one or more of the one or more electrical circuits.

27. The microfluidic system of claim 25, wherein the electrical circuits comprise an integrated circuit disposed in the microfluidic device.

28. The microfluidic system of claim 25, wherein the interface array of the controller instrument comprising two or more electrical contacts positioned to contact one or more of the electrical circuits to the a microfluidic device of the instrument.

29. A microfluidic system, comprising:

a controller instrument comprising a microfluidic device nesting region having an interface array for operably coupling one or more of a material transport system and a detector disposed within the controller instrument with a microfluidic device placed in the nesting region; and a microfluidic device having a body structure, the body structure comprising a mechanical indicator providing an indication to the controller instrument of a functionality of the microfluid device, the mechanical indicator element comprising a first registration structure having a first selected size or shape, and wherein the nesting region comprises a second registration structure that is complementary to the first registration structure.

30. The microfluidic system of claim 29, wherein positioning of the microfluidic device on the nesting region such that the registration structure on the microfluidic device and the complementary registration structure are joined, the microfluidic device is oriented to operably interface with the interface array.

31. The microfluidic system of claim 29, wherein the first selected shape is selected based upon an application for which the microfluidic device is intended.

32. The microfluidic system of claim 29, wherein the first registration structure is selected from a tab, a series of tabs, a pin, a series of pins, a hole disposed in the body structure, a series of holes in the body structure, a notch in the body, a series of notches in the body, and a shaped edge of the body.

33. A microfluidic system, comprising:

a controller instrument comprising a microfluidic device nesting region having an interface array for operably coupling one or more of a material transport system and a detector disposed within the controller instrument with a microfluidic device placed in the nesting region; and a microfluidic device having a body structure, the body structure comprising an indicator element that comprises an electrical indicator element comprising one or more electrical circuits disposed in the microfluidic device, the one or more circuits providing an electrical signature that is indicative of a functionality of the microfluidic device, wherein the interface array of the controller instrument comprises two or more electrical contacts positioned to contact one or more of the electrical circuits to indicate the functionality of the microfluidic device of the instrument the electrical signature comprising a number and identity of the two or more electrical contacts on the instrument that are connected by the one or more electrical circuits on the microfluidic device.

* * * * *

UNITED STATES PATENT AND TRADEMARK OFFICE
CERTIFICATE OF CORRECTION

PATENT NO.    : 6,495,104 B1
DATED         : December 17, 2002
INVENTOR(S)   : Unno et al.

It is certified that error appears in the above-identified patent and that said Letters Patent is hereby corrected as shown below:

Column 12,
Line 7, please delete "5" and insert -- 15 --.
Line 8, please delete "providing" and insert -- provides --.
Line 11, after "functionality" please insert -- of --.
Line 18, after "for" please insert -- use with --.
Line 37, after "and" please insert -- a --.
Line 41, after "indicator" please insert -- element --.
Line 47, after "21" please insert -- or 29 --.

Column 13,
Line 2, after "to" please insert -- indicate --.
Line 2, please delete "a" and insert -- functionality of the --.

Signed and Sealed this

Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO.      : 6,495,104 B1
DATED           : December 17, 2002
INVENTOR(S)     : Unno et al.

It is certified that error appears in the above-identified patent and that said Letters Patent is hereby corrected as shown below:

<u>Title page,</u>
Item [73], Assignee, after "US", please insert -- Agilent Technologies, Inc., Palo Alto, CA (US) --.

Signed and Sealed this

Fifth Day of August, 2003

JAMES E. ROGAN
*Director of the United States Patent and Trademark Office*